United States Patent [19]
Bernstein et al.

[11] Patent Number: 5,873,831
[45] Date of Patent: Feb. 23, 1999

[54] METHOD AND SYSTEM FOR MEASUREMENT OF MACULAR CAROTENOID LEVELS

[75] Inventors: Paul S. Bernstein; Werner Gellermann; Robert W. McClane, all of Salt Lake City, Utah

[73] Assignee: The University of Utah Technology Transfer Office, Salt Lake City, Utah

[21] Appl. No.: 815,936

[22] Filed: Mar. 13, 1997

[51] Int. Cl.[6] ........................................................ A61B 6/00
[52] U.S. Cl. .......................... 600/473; 600/475; 600/476; 600/477; 600/310
[58] Field of Search ..................................... 600/473, 476, 600/475, 477, 310, 318; 356/301, 303; 606/2–4, 10

[56] References Cited

U.S. PATENT DOCUMENTS

| | | | |
|---|---|---|---|
| 4,758,081 | 7/1988 | Barnes | 606/4 |
| 4,852,579 | 8/1989 | Gilstad et al. | 600/476 |
| 5,243,983 | 9/1993 | Tarr et al. | 128/633 |
| 5,275,168 | 1/1994 | Reintjes et al. | 600/476 |
| 5,418,797 | 5/1995 | Bashkansky et al. | 600/473 |

OTHER PUBLICATIONS

Schalch, Wolfgang, "*Carotenoids in the Retina—A Review of Their Possible Role in Preventing or Limiting Damage Caused by Light and Oxygen,*" Free Radicals and Aging, Basel, Switzerland: Birkhauser Verlag, pp. 280–298, 1992.

Seddon, J.M., Ajani, U.A., Sperduto, R.D., Hiller, R., Blair, N., Burton, T.C., Farber, M.D., Gragoudas, E.S., Haller, Jr., Miller, D.T., Yannuzzi, L.A., and Willet, W., "*Dietary Carotenoids, Vitamins A, C, and E, and Advanced Age–Related Macular Degeneration,*" J. Am. Med. Assoc., vol. 272, No. 18, pp. 1413–1420, Nov. 9, 1994.

Hammond, B.R., Fuld, K., and Curran–Celentano, J., "*Macular Pigments Density in Monozygotic Twins,*" Invest. Ophthalmol. Vis. Sci., vol. 36, No. 12, pp. 2531–2541, Nov., 1995.

Handelman, G.J., Snodderly, D.M., Krinsky, N.I., Russett, M.D., and Adler, A.J., "*Biological Control of Primate Macular Pigment,*" Inv. Ophthalmol. Vis. Sci., vol. 32, No. 2, pp. 257–267, Feb., 1991.

Bone, R.A., Landrum, J.T., and Cains, A., "*Optical Density Spectra of the Macular Pigment In Vivo and In Vitro,*" Vision Res., vol. 32, No. 1, pp. 105–110, 1992.

Brody, J.E., "*Health Factor in Vegetables Still Elusive,*" The New York Times, Section C, p. 1, Feb. 21, 1995.

*Primary Examiner*—Brian Casler
*Attorney, Agent, or Firm*—Workman, Nydegger & Seeley

[57] ABSTRACT

The present invention is directed to a new and useful method and apparatus for use in determining the levels of macular pigments in the tissue of live subjects. Specifically, the method and apparatus of the present invention provide a non-invasive, rapid, and objective determination of the macular carotenoid levels, and in turn, offer valuable diagnostic information applicable to large populations. The present invention measures the levels of macular carotenoid pigments, as well as other retinal materials. Monochromatic laser light is projected onto a retina, preferably in the macular area. A very sensitive detection system then detects light scattered from the retina. The majority of the light is scattered elastically at the same wavelength of the laser in a manner known as Rayleigh scattering. A very small fraction of laser light is scattered inelastically at a wavelength different from that of the laser in a manner known as Raman scattering. The Raman scattered light is selected and then routed to a detection system, wherein the results are calibrated against actual standards for the particular retinal material being tested.

32 Claims, 5 Drawing Sheets

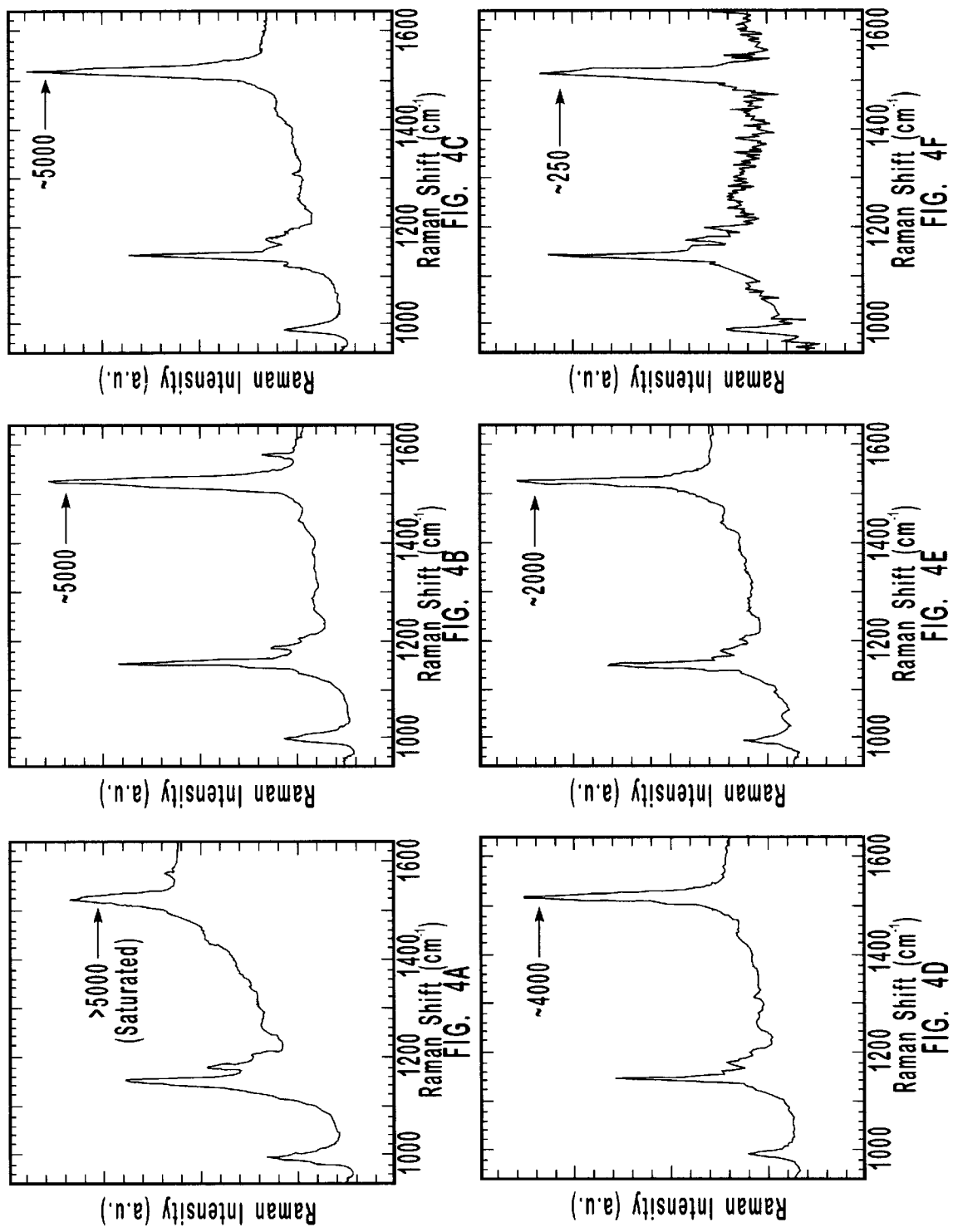

METHOD AND SYSTEM FOR MEASUREMENT OF MACULAR CAROTENOID LEVELS

BACKGROUND OF THE INVENTION

1. The Field of the Invention

The present invention relates generally to methods and apparatus for measuring levels of chemical compounds located in the anatomy of the eye, and more specifically to methods and apparatus for measuring such compounds in the eye for assessing the risk of suffering diseases of the eye.

2. The Relevant Technology

Vision, or sense of sight, is one's ability to perceive the form, color, size, movement, and distance of objects, by way of complex anatomy generally termed the eye. Vision occurs when light passes through the eye and is absorbed by the sensitive cells of the retina in the back of the eye. Specifically, light enters the cornea of the eye, passes through the pupil, and then through the lens, from which it is projected to the retina. Human vision in particular is sensitive for light in the visible spectrum, which is from approximately 380–720 nanometers in wavelength.

In order to actually see an image, the lens of the eye must bring the image into focus on the retina. Clear vision, or visual acuity, refers to the sharpness of the image and depends in part on the capability of the lens. The portion of the retina in which visual acuity is the greatest is called the fovea centralis. In the fovea centralis, light falls directly on individual photoreceptors, the sensory cells that respond electrically to light, whereas light in other regions of the retina must pass through several layers of nerve cells before reaching the photoreceptors.

Surrounding the fovea centralis is an area called the macula. The macula is less efficiently shielded from incoming light than other retinal tissue because there are fewer cell layers lying between the incoming light and the photoreceptors. The macula is typically yellow in color due to the presence of a high concentration of the carotenoids lutein and zeaxanthin. These carotenoids, which are normal constituents of a healthy diet, have been shown to offer statistically significant protection against age-related macular degeneration, the leading cause of irreversible blindness among the elderly in the United States. Lutein and zeaxanthin are actively concentrated in the macular tissue where it is believed they screen out phototoxic short wavelength visible light and act as free-radical scavenging antioxidants. It is believed that insufficient levels of these carotenoids permit photic and oxidative damage of the macular tissue.

It is possible to detect the levels of the macular carotenoids. One technique measures carotenoid levels in postmortem eye tissue utilizing conventional biochemical means such as high performance liquid chromatography (HPLC) and visible absorption spectrophotometry. However, this technique clearly suffers from the absence of any value for use in connection with live subjects.

The conventional technique for non-invasive measurement of human macular carotenoids is a "subjective psychophysical flicker photometric test" which involves color intensity matching of a light beam aimed at the fovea with one aimed at the parafoveal area of the retina. This technique is time-intensive and requires both highly sophisticated optical apparatus and highly skilled technicians. In addition, the patient must be alert, cooperative, and have relatively good visual acuity. Such requirements limit the usefulness of this technique for assessing macular carotenoids in an elderly population at risk for age-related macular degeneration, the very essence of which is a reduction in visual acuity. Elderly patients may face added frustration in an attempt to communicate the necessary information to the technician. Clearly, the conventional technique is not conducive for testing the levels of macular carotenoids in non-communicative patients and animals.

SUMMARY AND OBJECTS OF THE INVENTION

It is therefore a primary object of the present invention to provide methods and apparatus for rapid, non-invasive, and objective measurement of the levels of macular carotenoids in live subjects.

It is yet another object of the present invention to provide methods and apparatus which allow the information derived therefrom to be utilized to assess the risk of suffering from age-related macular degeneration.

Another object of the present invention is to provide methods and apparatus for measuring the levels of macular carotenoids such that the information derived therefrom is diagnostically valuable and applicable to a large population of live subjects.

Yet another object of the present invention is to provide methods and apparatus for measuring the levels of macular carotenoids which decreases the training, time, and expense of conventional methods.

Still another object of the present invention is to provide methods and apparatus for detecting and measuring the levels of other materials deposited and concentrated in retinal tissue.

To achieve the foregoing objects, and in accordance with the invention as embodied and broadly described herein, the present invention is directed to new and useful methods and apparatus for use in determining the levels of macular carotenoids and other materials in the tissue of live subjects. In particular, the methods and apparatus of the present invention provide a non-invasive, rapid, and objective determination of macular carotenoid levels. In turn, the present invention offers valuable diagnostic information applicable to large populations which may help in assessing the risk of developing age-related macular degeneration, and aid in determining preventative protocols.

The present invention quantitatively measures the levels of macular carotenoid pigments and other materials using the principles of Raman spectroscopy. Monochromatic laser light is directed onto the macular area of a retina. A very sensitive detection system then detects light scattered from the retina. The majority of the light is scattered elastically at the same wavelength of the laser. A very small fraction of laser light is scattered inelastically at a wavelength different from that of the laser. The scattered light is then routed to a detection system wherein the inelastically scattered light is selectively filtered and measured. The results are calibrated against actual standards for macular carotenoids or the particular retinal material being tested.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to a specific embodiment thereof which is illustrated in the appended drawings. Understanding that these drawings depict only a typical embodiment of the invention and are not therefore to be considered to be limiting of its scope, the invention in its presently understood best mode for making and using the same will be described and explained with additional specificity and detail through the use of the accompanying drawings in which:

FIGS. 4A–F4 are is a graphic representations of Raman signal strength determined at various distances from the center of the macula.

DETAILED DESCRIPTION OF THE PREFERRED EMBODIMENTS

Figure 1:
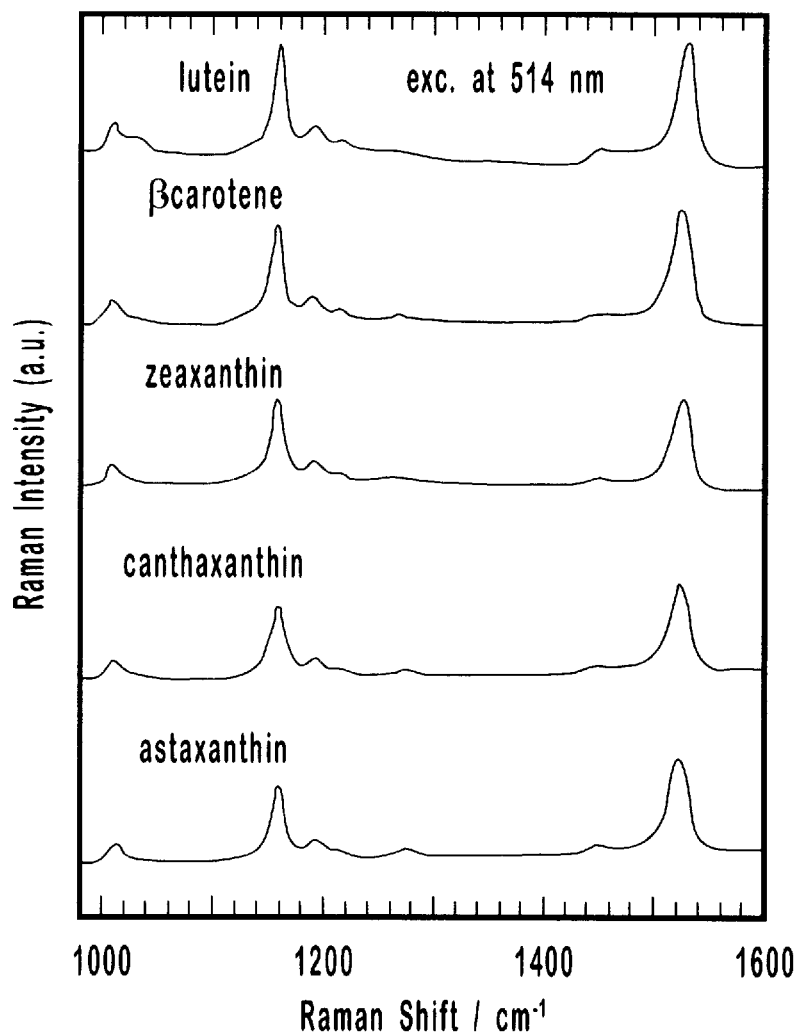
FIG. 1 is a graphic representation of Raman Spectra of selected carotenoids.

The fastest growing segment of the United States population comprises persons older than 65 years. The leading cause of irreversible blindness in this same group is due to age-related degeneration of the macula, the visual acuity center of the retina. Therefore, it is likely that along with the increase in the elderly population, the prevalence and impact of age-related macular degeneration will also increase. The benefits derived from prevention or retardation of the onset of age-related macular degeneration would therefore have a major beneficial effect on this growing population.

It has been demonstrated that the carotenoids lutein and zeaxanthin may significantly prevent age-related macular degeneration by screening out damaging short wavelength visible light and acting as free-radical scavenging antioxidants. It would be a significant benefit to ascertain the levels of lutein and zeaxanthin before the subject exhibits symptoms of visual impairment or blindness.

There currently exist two primary techniques for evaluating the levels of macular carotenoids. One technique objectively measures carotenoid levels in post-mortem eye tissue utilizing conventional biochemical means such as high performance liquid chromatography (HPLC) and visible absorption spectrophotometry. However, this mechanism suffers from the absence of any preventative value or practical application that would benefit the actual subject from whom the post-mortem eye tissue was obtained.

The second conventional technique for evaluating the levels of macular carotenoids requires the patient to match the color intensity of a light beam aimed at the fovea with one aimed at the parafoveal area of the retina. This technique is time intensive and requires both highly sophisticated optical apparatus and highly skilled technicians. In addition, the patient must be alert, cooperative, and have relatively good visual acuity. Such requirements limit the usefulness of this technique for assessing macular carotenoids in an elderly population at risk for age-related macular degeneration, the very essence of which is a reduction in visual acuity. Elderly patients may face added frustration in an attempt to communicate the necessary information to the technician. Furthermore, the conventional technique is not conducive for testing non-communicative patients or animals. This technique suffers from the lack of objective standards and is imprecise at best.

The present invention, which relates to methods and apparatus for assessing a subject's risk for suffering from diseases relating to the macular tissue in the eye, solves the problems encountered with the prior techniques. In particular, the methods and apparatus of the present invention provide a non-invasive, rapid, and objective determination of the macular carotenoid levels in live subjects. In turn, the present invention offers valuable diagnostic information applicable to large populations which may help in assessing an individual's risk of developing age-related macular degeneration, and in determining protocols for prevention of the same.

In a technique referred to as laser Raman spectroscopy, monochromatic laser light is directed onto a particular material to be tested. A very sensitive detection system then detects light returning, or scattered, from the material. The majority of the light returning from the material is scattered elastically at the same wavelength of the original projected laser light in a manner known as Rayleigh scattering. A very small fraction of the light returning from the material is scattered inelastically at a wavelength different from that of the original projected laser light in a manner known as Raman scattering. Raman scattered light is then separated from Rayleigh scattered light with the use of filters, optical gratings, prisms, and other wavelength selection techniques.

The energy difference between Raman and Rayleigh scattered light, represented in wave numbers ($cm^{-1}$), is related to the vibrational, rotational, or liberational states, or mixtures thereof, of various molecules in the material being evaluated. Each of the peaks in the resulting Raman spectrum corresponds to a particular Raman active vibration of a molecule or a component thereof. The Raman energy shift is independent of the wavelength of the directed laser light. That is, the energy difference corresponding to the elastically and inelastically scattered light for a particular material remains constant for that material.

The characteristic results from Raman scattering can be used to locate, identify and quantitate concentrations of a material. The absolute intensities of the resulting Raman peaks are directly related to the concentration of the Raman-active molecules in the material. The macular carotenoids lutein and zeaxanthin have been found to exhibit characteristic Raman scattering, the results of which show up in distinct spectral positions, signal strengths, and spectral widths. More specifically, lutein and zeaxanthin exhibit strong characteristic Raman scattering signals near 1160 and 1520 $cm^{-1}$, and weaker signals near 1000 $cm^{-1}$, as graphically illustrated in FIG. 1. Further, isolation of any one or all resultant Raman peaks is possible. Additionally, lutein and zeaxanthin demonstrate a resonance Raman scattering amplification when excited by laser light in a range which overlaps with their respective absorption bands, such as from 450 to 550 nanometers.

Yet, the utilization of a low power laser, such as a 1 milliwatt visible laser excitation source, typically results in extremely weak Raman scattering in comparison with the strength of the laser excitation source. In addition, the Raman signals are often overwhelmed by the much stronger signals originating from fluorescence of the same or other materials. It was therefore unexpected to direct a low power laser light into the macula of an eye and still generate usable Raman signals.

It is a feature of the present invention to provide methods and apparatus for measuring macular carotenoids in live subjects utilizing Raman spectroscopy such that retinal exposure to low laser power generates a usable macular carotenoid Raman signal without significant damage to the macular tissue. It should also be understood that the methods and apparatus of the present invention may also be utilized to detect other materials present in retinal tissue.

Figure 3:
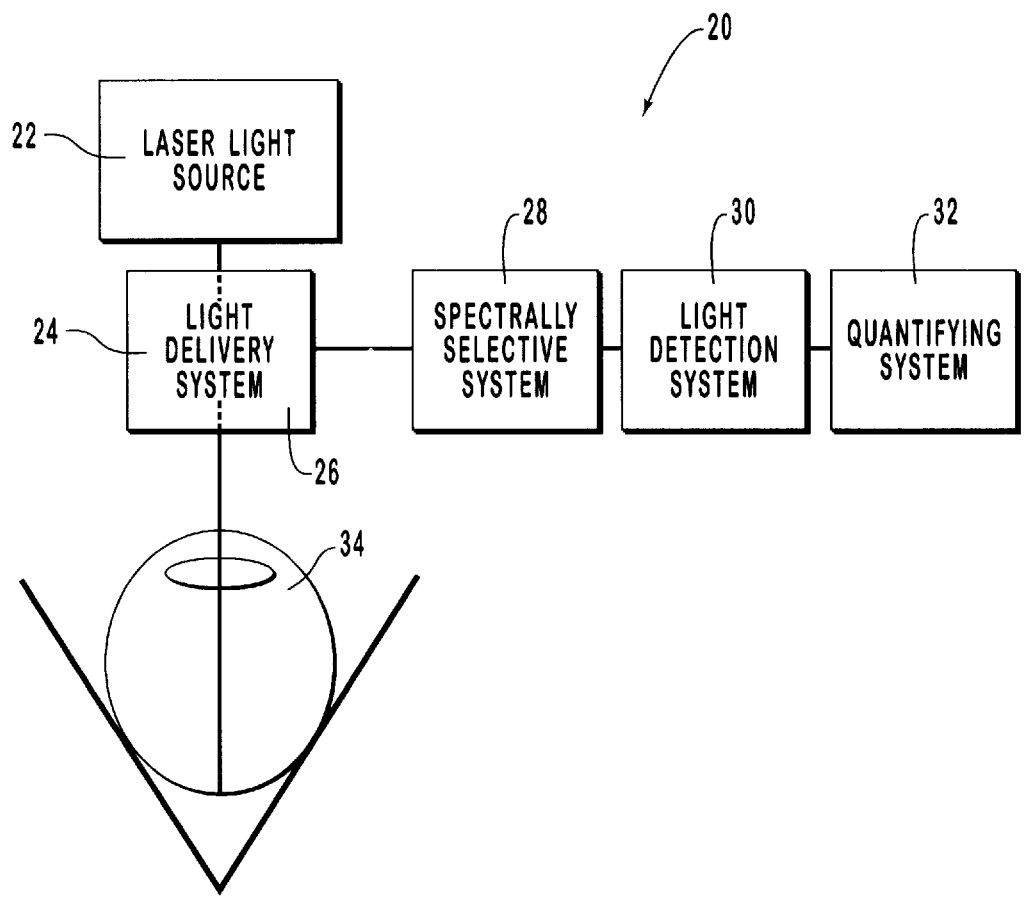
FIG. 3 is a schematic representation of the apparatus of the present invention.

In the presently preferred embodiment of the present invention, FIG. 3 depicts a schematic illustration of an apparatus, generally labelled 20, for measuring macular carotenoids. Preferably, the apparatus of the present invention generates light from a laser light source 22. Alternatively, other means for generating light would be within the scope of the present invention, including, but not limited to light sources that generate monochromatic light, and any other light projection system.

In a preferred embodiment of the present invention, laser light source 22 generates laser light in the 450 to 550 nm range, which corresponds to the absorption characteristics for macular carotenoids. However, it should be understood that the present invention is not limited to generated light between these wavelengths. For example, other wavelengths of generated light would be effective with the apparatus of the present invention.

The generated light is preferably directed to the subject eye 34 via a generated light delivery system 24. It should be appreciated, however, that various delivery means for directing the generated light would be within the scope of the present invention. For example, one preferred delivery means for directing generated light is a slit lamp. Other preferred delivery means include, but are not limited to direct ophthalmoscopes and mirrors. Alternatively, the delivery means for directing generated light may incorporate a small beam scanned across the macular area in a manner analogous to the method used in the scanning laser ophthalmoscope or optical coherence tomography, both of which should be familiar to those of skill in the art.

The light directed at the retina is limited to a maximum permissible exposure dose, one example of which is equivalent to a laser power of 1 milliwatt, spot size 1 mm, and exposure time of 10 seconds, which is safe and sufficient. It should be appreciated that other power, size, and exposure times are also within the scope of the present invention, in as much as they fall within safety limits for retinal tissue. The present invention specifically envisions significantly decreased exposure doses and times.

The returning light scattered from the macular area is moderately focused by the lens of the eye and emitted through the pupil, whereinafter it is then collected via a light collection system 26. In a preferred embodiment illustrated in FIG. 3, light collection system 26 is incorporated structurally with light delivery system 24. In an alternate embodiment, light collection system may be structurally separated from light delivery system.

It should also be appreciated that other light collection means for collecting the returning light scattered from the retina would be within the scope of the present invention. Such light collection means include optical fibers, lenses, mirrors, and combinations thereof.

The scattered light is then routed to a spectrally selective system 28 which selects only the Raman scattered light and rejects the Rayleigh scattered light, such that the Raman signals may be analyzed absent interference from Rayleigh signals. It should be understood that any spectrally selective means for filtering scattered light which is able to filter elastically scattered light from inelastically scattered light would be within the scope of the present invention. One preferred spectrally selective means is a grating monochromator. Other examples include, but are not limited to, holographic filters, prisms, dielectrics, or combinations thereof.

After the scattered light is spectrally selected, it is channeled to a light detection system 30 which measures the intensity of the scattered light as a function of wavelengths in the region of Raman peaks around 1160 and 1520 $cm^{-1}$, characteristic of macular carotenoids. In alternative embodiments, other light detection means for measuring the intensity of the scattered light such as a CCD, photomultiplier, or any other sensitive photo detector such as a photodiode, would also be within the scope of the present invention.

In a preferred embodiment, light detection system 30 converts the scattered light signal for visual display on a visual display means such as a computer monitor or other similar screen. It should be understood, however, that light detection system 30 may convert the scattered light signal into a format for numerical, digital, or other form for detection.

The resultant Raman signal intensity is preferably analyzed via a quantifying system 32 which may be calibrated by comparison against chemically measured carotenoid levels in human post-mortem eyes or by experiments on non-human primates. Other quantifying methods for calibrating Raman signal intensity would also be within the scope of the present invention.

To use the apparatus of the present invention, the first step preferably includes generating light from a laser light source 22, as depicted in FIG. 3. The light is preferably generated in the 450 to 550 nm range, which corresponds to the absorption characteristics for macular carotenoids. The generated light is next preferably directed to the subject eye 34 via a generated light delivery system 24. The directing of the light onto the macular area of the subject may be further achieved by having the subject fixate on the light or by direct confirmation by the operator via a suitable optical system. The light is selectively directed in order to cover a major area of macular carotenoid pigment deposition.

The returning light scattered from the macular area is then collected via a light collection system 26. The scattered light is then routed to a spectrally selective system 28 which selects only the Raman scattered light and rejects the Rayleigh scattered light, such that the Raman signals may be analyzed absent interference from Rayleigh signals. After the scattered light is spectrally selected, it is channeled to a light detection system 30 which measures the intensity of the scattered light as a function of wavelengths in the region of Raman peaks around 1160 and 1520 $cm^{-1}$, characteristic of macular carotenoids. The light detection system 30 then converts the scattered light signal for visual display on a visual display means such as a computer or other similar screen. The resultant Raman signal intensity is analyzed via a quantifying display system 32 which calibrates the results with actual carotenoid levels preferably through the examination of human post-mortem eyes or by experiments on non-human primates.

Studies were performed that demonstrate that strong Raman signals for the macular carotenoids are readily obtainable from human retinal tissue using low light exposure doses. It is expected that retinal irradiance could be further decreased with continued optimization of the signal collection system. The following examples detail the experimental procedures and the results derived therefrom.

1. EXAMPLE 1

A 6 milliwatt 0.5 mm argon laser spot (488 or 514 nm) was aimed for 9 seconds at the fovea of a flat-mounted human retina. The fovea, at the center of the macula, contains the highest concentration of the macular carotenoids. Scattered laser light was collected and analyzed by a commercial grating monochromator, such as a Spex Triple-mate, employing a cryogenically cooled CCD array. Calibration of signal intensity with actual carotenoid levels was achieved through the examination of human or primate post-mortem eyes.

FIG. 4, graph A, depicts a strong Raman spectrum characteristic of the macular carotenoids at the fovea, superimposed on a weak fluorescence background. As the laser spot was moved eccentrically from the fovea as illustrated in FIG. 4, graphs B through F, the Raman signal became progressively weaker. In fact, as illustrated in graph F, by the time the laser was 3 mm from the fovea, the strength of the Raman signal decreased by at least a factor of 20. This demonstrated sufficient sensitivity to detect the variation in macular carotenoid concentrations in closely adjacent anatomy.

2. EXAMPLE 2

Figure 5A:
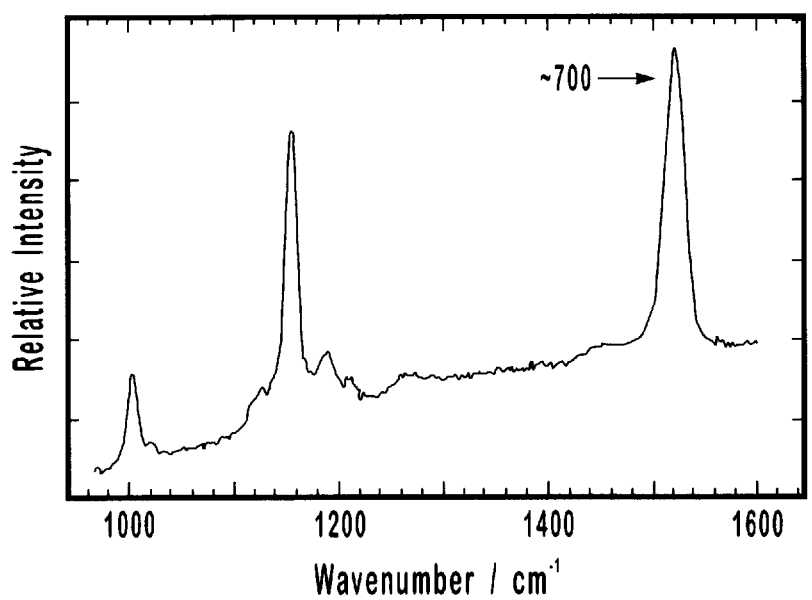
FIG. 5(a) is a graphic representation of Raman signal strength at the center of the macula.

A low power 2 milliwatt 514 nm argon laser spot 1.5 mm in diameter was aimed for 5 seconds at the center of the macula of a human eye cup. A characteristic macular carotenoid Raman spectrum was obtained, as graphically illustrated by FIG. 5(a).

Figure 5B:
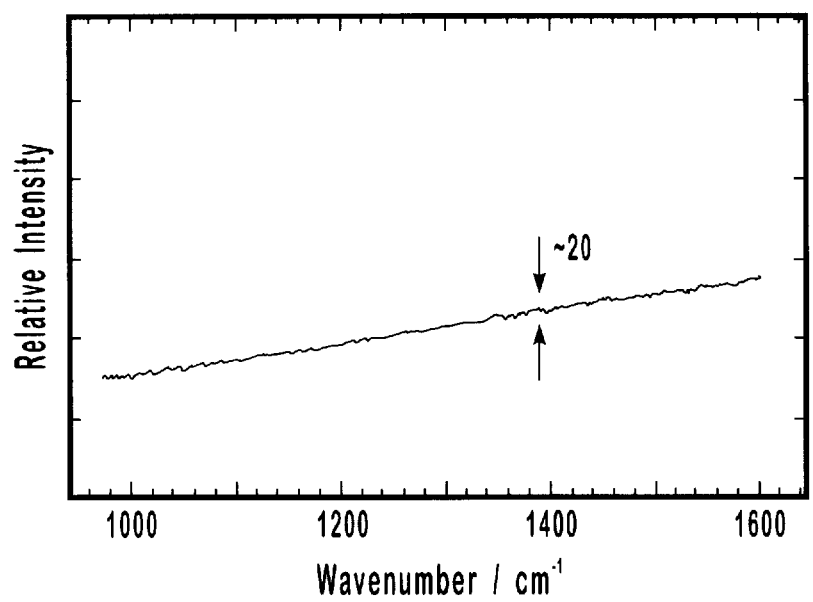
FIG. 5(b) is a graphic representation of Raman signal strength outside the center of the macula.

The same experiment performed on retinal tissue outside the macula depicted no Raman signal, as illustrated graphically by FIG. 5(b). This demonstrated that other ocular tissues including vitreous, retinal pigment epithelium, choroid, and sciera do not generate detectable Raman scattering under the experimental conditions. In addition, in example 2, the low (2 milliwatt) laser power still generated a detectable Raman signal.

3. EXAMPLE 3

As provided in the detailed description above, a 1 milliwatt or lower power monochromatic laser light in the 450 to 550 nm is directed to a subject's macular area for several seconds at a spot size of 1 mm. The light scattered from the macular area is then collected via an optical fiber and routed to a spectrally selective system, which filters out the Rayleigh scattered light and selects the Raman scattered light. A light detection system then scans and measures the intensity of the Raman shifted light at the frequencies characteristic of macular carotenoids, from approximately 1160 to 1520 $cm^{-1}$. The image is then converted for visual display on a computer monitor. Calibration of signal intensity with actual carotenoid levels is achieved through the examination of human or primate post-mortem eyes.

Figure 2:
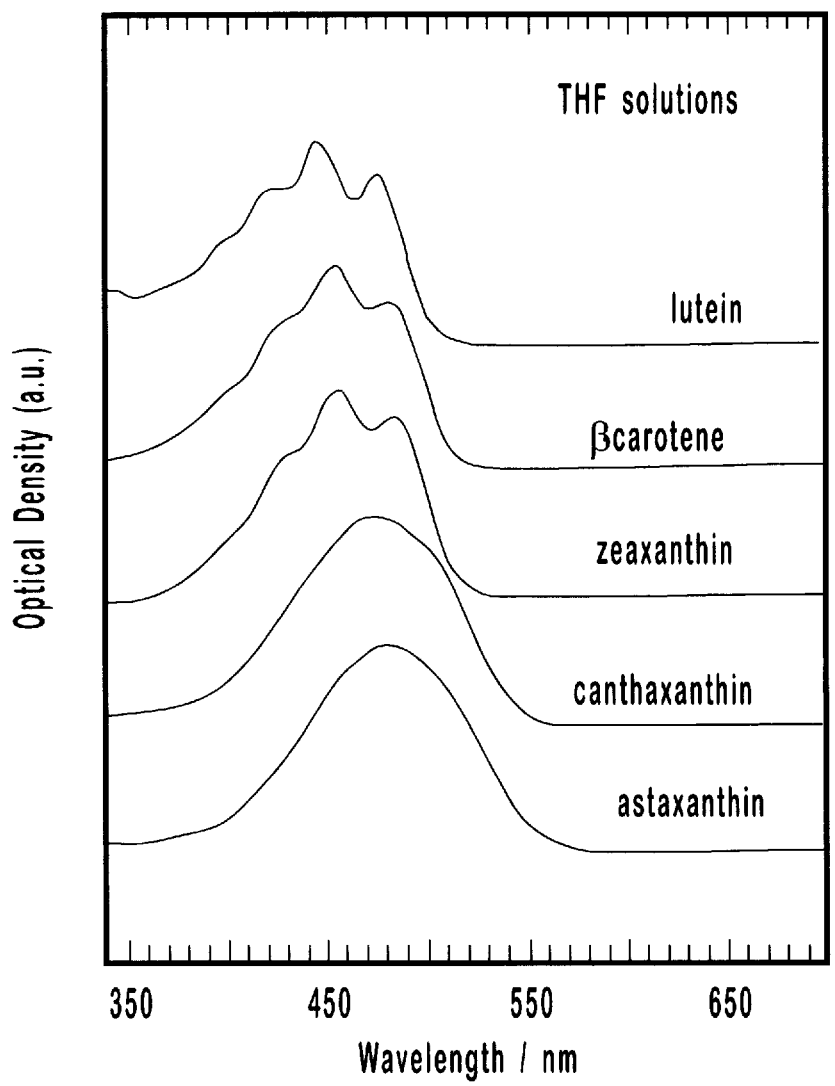
FIG. 2 is a graphic representation of Absorption Spectra of the carotenoids of FIG. 1.

It should be appreciated that the present invention ultimately offers a major advance in the study of age-related macular degeneration and other inherited and acquired retinal degenerations. It should be understood that the present method is not limited to detection of macular carotenoids. The method of the present invention is also particularly applicable to the measurement of β-carotene and pharmacological agents such as canthaxanthin, astaxanthin, chloroquine, hydroxychloroquine, thioridazine, and tamoxifen, which are concentrated and deposited within the retina. FIGS. 1 and 2 additionally graphically illustrate the Raman Spectra and Absorption Spectra, respectively, of β-carotene, canthaxanthin, and astaxanthin, and show that Raman enhanced scattering would be possible for those compounds.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for measurement of macular carotenoid levels comprising the steps of:
   a. obtaining a light source which generates light at a wavelength that produces a Raman response with a wavelength shift for a macular carotenoid to be detected;
   b. directing light from said light source onto macular tissue of an eye for which macular carotenoid levels are to be measured, said light having an intensity which does not cause photocoagulation or destruction of said macular tissue and does not alter said macular carotenoid levels;
   c. collecting light scattered from said macular tissue, said scattered light including elastically and inelastically scattered light, said inelastically scattered light having a quantifiable intensity;
   d. filtering out said elastically scattered light; and
   e. quantifying the intensity of said inelastically scattered light.

2. A method as recited in claim 1, wherein said light source generates light in a wavelength range from 450–550 nm.

3. A method as recited in claim 1, wherein said light source generates light in a wavelength which overlaps the absorption bands of said macular carotenoid to be detected.

4. A method as recited in claim 1, wherein said macular tissue resides in a live subject.

5. A method as recited in claim 1, wherein said scattered light is filtered via a spectrally selective means for filtering elastically scattered light from inelastically scattered light.

6. A method as recited in claim 5, wherein said spectrally selective means is a grating monochromator.

7. A method as recited in claim 5, wherein said spectrally selective means is a holographic filter.

8. A method as recited in claim 1, wherein said scattered light is measured at frequencies characteristic of macular carotenoids.

9. A method as recited in claim 1, wherein said inelastically scattered light is quantified via signal intensity calibrated with actual macular carotenoid levels.

10. A method as recited in claim 9, wherein said actual carotenoid levels are derived from examination of human post-mortem eyes.

11. A method as recited in claim 9, wherein said actual carotenoid levels are derived from experiments on non-human primates.

12. A method for detection of materials deposited and concentrated in retinal tissue comprising the steps of:
   a. obtaining a light source which generates light at a wavelength that generates a Raman response with a wavelength shift for a material to be detected;
   b. directing light from said laser onto retinal tissue of an eye for which levels of said material are to be measured, said light having an intensity which does not destroy said retinal tissue and does not alter the levels of said material;
   c. collecting light scattered from said retinal tissue, said scattered light including elastically and inelastically scattered light, said inelastically scattered light having a quantifiable intensity;

d. filtering out said elastically scattered light; and e. quantifying the intensity of said inelastically scattered light.

13. A method as recited in claim 12, wherein said light source generates light in a wavelength range from 450–550 nm.

14. A method as recited in claim 12, wherein said light source generates light in a wavelength which overlaps the absorption bands of said material to be detected.

15. A method as recited in claim 12, wherein said retinal tissue resides in a live subject.

16. A method as recited in claim 12, wherein said scattered light is filtered via a spectrally selective means for filtering elastically scattered light from inelastically scattered light.

17. An apparatus for non-invasive measurement of macular carotenoid levels comprising:

a. means for generating light within a wavelength giving a Raman response with a wavelength shift for the macular carotenoid being detected;

b. delivery means for directing said light onto the macula of an eye, said light having an intensity which does not damage said macula and which does not alter said macular carotenoid levels;

c. collection means for collecting light scattered from said macula;

d. spectrally selective means for selecting Raman shifted light from the scattered light collected by said collection means; and e. detection means for scanning and measuring said Raman shifted light at frequencies characteristic of macular carotenoids.

18. An apparatus as recited in claim 17, wherein said means for generating light is a laser beam.

19. An apparatus as recited in claim 17, wherein said means for generating light generates light in the range of 450 to 550 nm.

20. An apparatus as recited in claim 17, wherein said means for generating light generates light in a wavelength which overlaps the absorption bands of the carotenoid being detected.

21. An apparatus as recited in claim 17, wherein said means for generating light comprises a light exposure equivalent to a laser power of 1 milliwatt.

22. An apparatus as recited in claim 17, wherein said means for generating light comprises a light exposure spot size of 1 mm.

23. An apparatus as recited in claim 17, wherein said means for generating light comprises a light exposure time of ten seconds.

24. An apparatus as recited in claim 17, wherein said delivery means comprises a direct ophthalmoscope.

25. An apparatus as recited in claim 17, wherein said delivery means comprises a slit lamp.

26. An apparatus as recited in claim 17, wherein said collection means comprises an optical fiber.

27. An apparatus as recited in claim 17, wherein said spectrally selective means comprises a grating detector.

28. An apparatus as recited in claim 17, wherein said spectrally selective means comprises a holographic filter.

29. An apparatus as recited in claim 17, wherein said Raman shifted light is quantified.

30. An apparatus as recited in claim 29, wherein said quantified Raman shifted light is calibrated.

31. An apparatus for non-invasive detection of material deposited and concentrated in retinal tissue comprising:

a. means for generating light within a wavelength giving a Raman response with a wavelength shift for the material being detected;

b. delivery means for directing said light onto the retina of an eye, said light having an intensity which does not damage said retina and which does not alter the concentration of the material being detected;

c. collection means for collecting light scattered from said retina;

d. spectrally selective means for selecting Raman shifted light from the scattered light collected by said collection means;

e. detection means for scanning and measuring said Raman shifted light at frequencies characteristic of said material being detected; and f. quantifying means for determining Raman signal intensity for said material being detected.

32. An apparatus as recited in claim 29, wherein said means for generating light generates light in a wavelength which overlaps the absorption bands of the material being detected.

* * * * *

UNITED STATES PATENT AND TRADEMARK OFFICE
CERTIFICATE OF CORRECTION

PATENT NO. : 5,873,831
DATED : Feb. 23, 1999
INVENTOR(S) : Paul S. Bernstein; Werner Gellermen; Robert W. McClane It is certified that error appears in the above-identified patent and that said Letters Patent is hereby corrected as shown below:

Col. 7, line 16, after "of" change "20" to --20--

Col. 7, line 31, after "and" change "sciera" to --sclera--

Signed and Sealed this

Fourteenth Day of December, 1999

Attest:

Q. TODD DICKINSON

Attesting Officer

Acting Commissioner of Patents and Trademarks